United States Patent
Büyüktimkin et al.

(12) 
(10) Patent No.: US 6,414,028 B1
(45) Date of Patent: *Jul. 2, 2002

(54) TOPICAL COMPOSITIONS CONTAINING PROSTAGLANDIN $E_1$

(75) Inventors: Servet Büyüktimkin; Nadir Büyüktimkin, both of Lawrence, KS (US); James L. Yeager, Deerfield, IL (US)

(73) Assignee: NexMed Holdings, Inc., Robbinsville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/542,668

(22) Filed: Apr. 4, 2000

Related U.S. Application Data

(60) Provisional application No. 08/964,509, filed on Nov. 5, 1997, now Pat. No. 6,046,244.

(51) Int. Cl.[7] .......................... A01N 37/08; A01N 53/00; A01N 25/00; A61K 47/00
(52) U.S. Cl. ...................... 514/573; 514/785; 514/946; 514/947; 514/782
(58) Field of Search ................................. 514/573, 785, 514/946, 947; 560/121

(56) References Cited

U.S. PATENT DOCUMENTS

| | | | |
|---|---|---|---|
| 4,661,524 A | 4/1987 | Thomson et al. | 514/682 |
| 4,731,241 A | 3/1988 | Yamada et al. | 514/236.2 |
| 4,732,892 A | 3/1988 | Sarpotdar et al. | 514/178 |
| 4,771,004 A | 9/1988 | Higuchi | 436/5 |
| 4,808,414 A | 2/1989 | Peck et al. | 424/449 |
| 4,865,848 A | 9/1989 | Cheng et al. | 424/449 |
| 4,973,468 A | 11/1990 | Chiang et al. | 424/449 |
| 4,980,378 A | 12/1990 | Wong et al. | 514/785 |
| 5,082,866 A | 1/1992 | Wong et al. | 514/785 |
| 5,413,794 A | 5/1995 | Suzuki et al. | 424/449 |
| 5,534,260 A | 7/1996 | Petersen et al. | 424/448 |
| 5,534,554 A | 7/1996 | Katz et al. | 514/724 |
| 5,942,545 A * | 8/1999 | Samour et al. | 514/573 |
| 6,046,244 A * | 4/2000 | Buyuktimkin et al. | 514/785 |
| 2001/0019721 A1 * | 9/2001 | Brandt et al. | 424/443 |

OTHER PUBLICATIONS

Uekama et al. Improved Tranderdmal Delivery of Prostaglandin $E_1$ Through Hairless Mouse Skin: Combined Use of Carboxymethyl–ethyl–beta–cyclodextrin and Penetration Enhancers, Journal of Pharmaceutical Pharmacology, Freb. 1992. vol. 44, No. 2, pp. 119–121.

Adachi et al. Inhibitory Effect of Prostaglandin $E_1$ on Laurate–Induced Peripheral Vascular Occlusive Sequelae in Rabbits: Optimized Topical Formulation with Beta–Cyclodextrin Derivative and Penetration Enhancer HPE–101, Journal of Pharmaceutical Pharmacology Dec. 1992. vol. 44, No. 12, pp. 1033–1035.

Article, "Alkyl N,N–Disubstituted–Amino Acetates", Büyüktimkin, N., et al., pp. 91–102, appearing in "Percutaneous Penetration Enhancers," 1995 by CRC Press, Inc.

Abstract No. 2686, 1997 AAPS Annual Meeting Contributed Papers Abstracts, American Association of Pharmaceutical Scientists.

* cited by examiner

*Primary Examiner*—Dameron L. Jones
*Assistant Examiner*—Lauren Q. Wells
(74) *Attorney, Agent, or Firm*—Olson & Hierl, Ltd.

(57) ABSTRACT

A topical composition of a semi-solid consistency suitable is provided for transdermal application of prostaglandin $E_1$. The composition comprises prostaglandin $E_1$, a penetration enhancer, a polysaccharide gum, a lipophilic compound, and an acidic buffer system. The penetration enhancer is an acid addition salt of an alkyl-2-(substituted amino)-alkanoate ester, of a (substituted amino)-alkanol alkanoate, or of a mixture thereof. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4.

29 Claims, 4 Drawing Sheets

TOPICAL COMPOSITIONS CONTAINING PROSTAGLANDIN E₁

CROSS-REFERENCE TO RELATED APPLICATION

This application is a continuation-in-part of U.S. Ser. No. 08/964,509 filed on Nov. 5, 1997, now U.S. Pat. No. 6,046,244.

TECHNICAL FIELD OF THE INVENTION

This invention relates to pharmaceutical compositions for transdermal administration of prostaglandin drugs to a patient.

BACKGROUND OF THE INVENTION

Prostaglandin $E_1$ is a derivative of prostanoic acid, a 20-carbon atom lipid acid, represented by the formula:

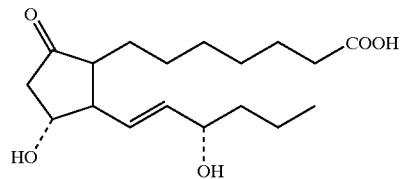

and is commercially available, e.g., from Chinoin Pharmaceutical and Chemical Works Ltd. (Budapest, Hungary) under the designation "Alprostadil USP" and from The Upjohn Company (Kalamazoo, Mich.) under the designation "Prostin VR."

Prostaglandin $E_1$ is a vasodilator useful to maintain open blood vessels and therefore, to treat peripheral vascular disease among other ailments. While the potential benefits from transdermal delivery of prostaglandin $E_1$ have long been recognized, prior efforts at developing a topical composition for prostaglandin delivery have not been fully successful.

In particular, there is presently no commercial source for a topical semi-solid formulation that is useful without a supporting device such as a patch, adhesive strip, and the like. For example, U.S. Pat. No. 5,380,760 to Wendel et al. is directed to a topical prostaglandin formulation that includes a pressure-sensitive, adhesive sheet of polyisobutylene.

Working alone most drugs, prostaglandin formulations included, do not sufficiently permeate the skin to provide drug concentration levels comparable to those obtained from other drug delivery routes. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not affect available dosage forms (e.g. cream or gel), or cosmetic quality of the topical composition.

A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Büyüktimkin et al., Chemical Means of Transdermal Drug Permeation Enhancement in *Transdermal and Topical Drug Delivery Systems*, Gosh T. K., Pfister W. R., Yum S. I. (Eds.), Interpharm Press Inc., Buffalo Grove, Ill. (1997).

A fully successful formulation for prostaglandin $E_1$ has not yet been identified. Unfortunately, prostaglandin $E_1$ is readily transformed by rearrangement and other reactions. This relative instability tends to complicate efforts at formulating composition for transdermal delivery.

The present invention addresses these problems by providing a semi-solid, separation resistant composition for relatively rapid, sustained delivery of prostaglandin $E_1$.

SUMMARY OF THE INVENTION

A pharmaceutical composition suitable for topical application comprises prostaglandin $E_1$, a penetration enhancer, a polysaccharide gum, a lipophilic compound, and an acidic buffer system. The penetration enhancer can be an alkyl-2-(substituted amino)-alkanoate ester, a (substituted amino)-alkanol alkanoate, a mixture of these, or an acid addition salt thereof. The acid can be organic or inorganic. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4. If desired, stabilizers and emulsifiers may be included.

Compositions of the present invention can take the form of a semi-solid suitable for topical application. In use as a topical agent, these compositions exhibit relatively high prostaglandin penetration and bioavailability without requiring a wasteful overloading prostaglandin concentration. The compositions further exhibit reduced skin irritation, sensitivity and damage.

Other and further aims, purposes, features, advantages, embodiments and the like will be apparent to those skilled in the art from the present specification and the appended claims.

DETAILED DESCRIPTION OF THE INVENTION

Figure 1:
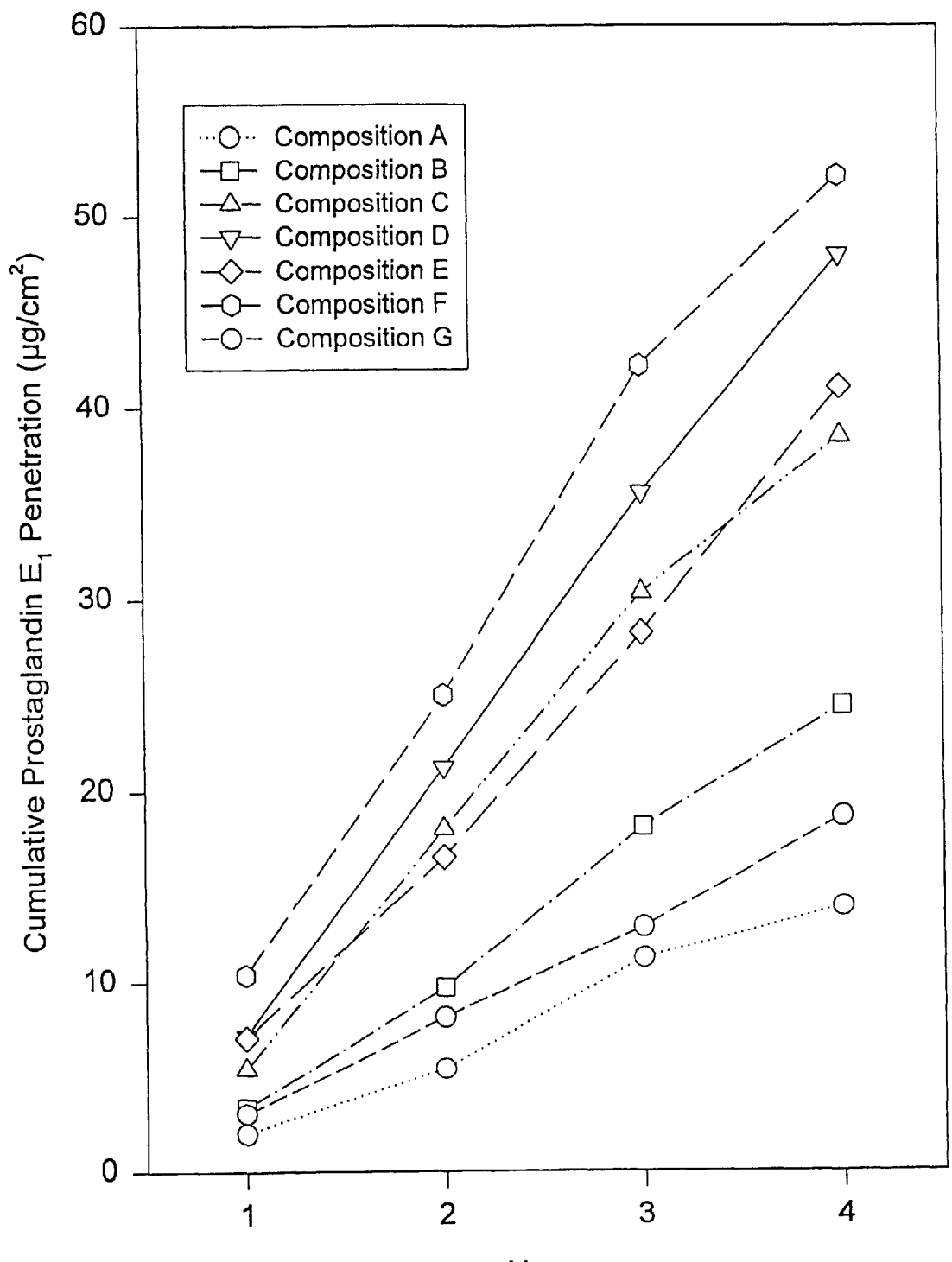
FIG. 1 is a graph of the cumulative prostaglandin $E_1$ penetration through shed snake skin of seven prostaglandin $E_1$ compositions prepared according to the present invention.
Figure 2:
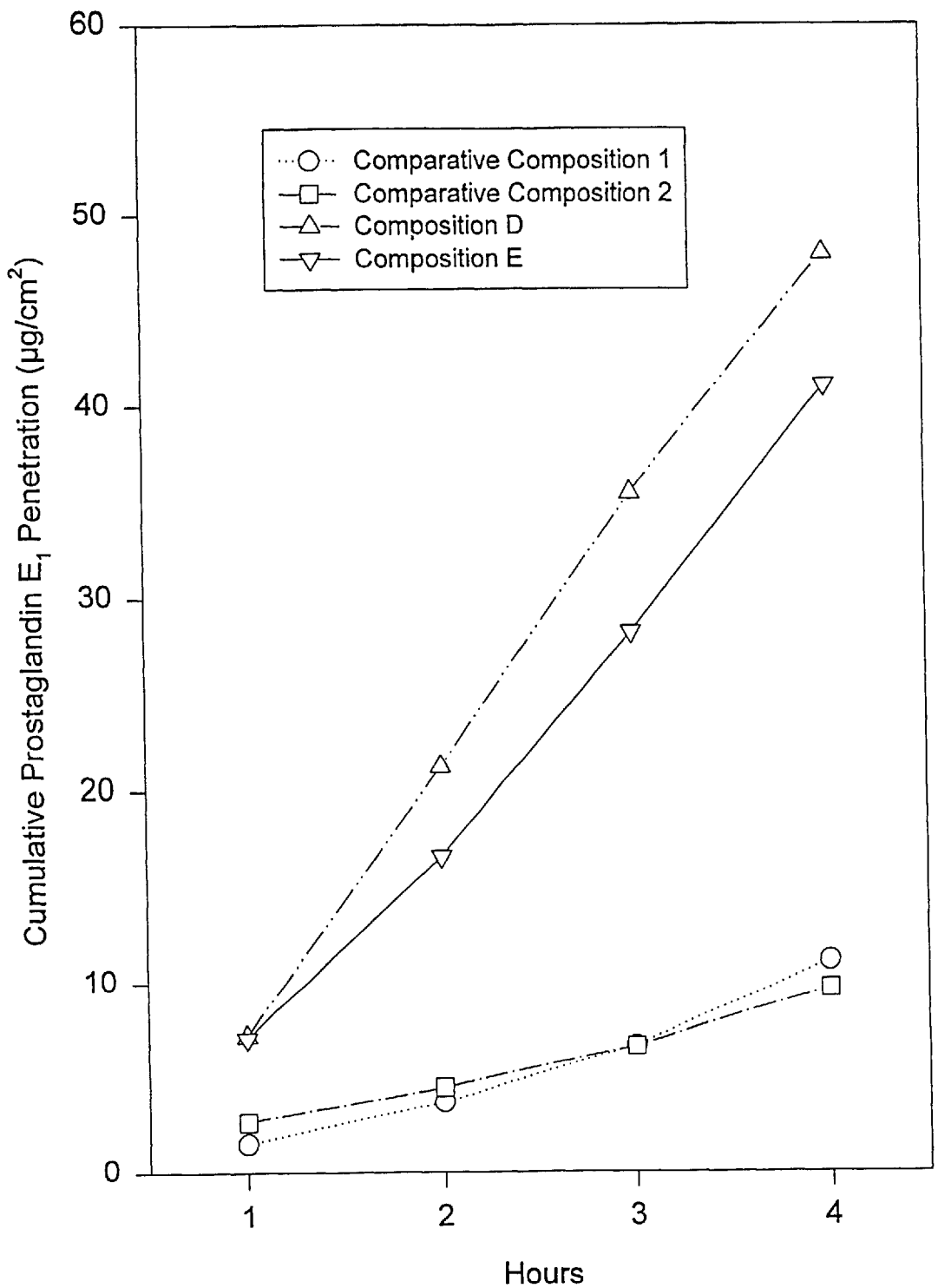
FIG. 2 is a comparison graph of the cumulative prostaglandin $E_1$ penetration through shed snake skin of two prostaglandin $E_1$ compositions prepared according to the present invention and two comparative compositions.

The pharmaceutical composition of the present invention comprises prostaglandin $E_1$, an acid addition salt of an alkyl (substituted amino) ester, a polysaccharide gum, a lipophilic compound, and an acid buffer system.

Prostaglandin $E_1$ is well known to those skilled in the art. Reference may be had to various literature references for its pharmacological activities, side effects, and normal dosage ranges. See for example, *Physician's Desk Reference*, 51st Ed. (1997), *The Merck Index*, 12th Ed., Merck & Co., N.J. (1996), and *Martindale The Extra Pharmacopoeia*, 28th Ed., London, The Pharmaceutical Press (1982). Prostaglandin $E_1$ as well as other compounds referenced herein are intended to encompass pharmaceutically acceptable derivatives including physiologically compatible salts and ester derivatives thereof.

The quantity of prostaglandin $E_1$ in the pharmaceutical compositions of the present invention is a therapeutically effective amount and necessarily varies according to the desired dose, the dosage form (e.g., suppository or topical), and the particular form of prostaglandin $E_1$ used. The composition generally contains between 0.1 percent to 1 percent prostaglandin $E_1$, preferably from 0.3 percent to 0.5 percent, based on the total weight of the composition.

An important component of the present invention is the penetration enhancer.

Alkyl-2-(substituted amino) -alkanoates suitable as penetration enhancers for purposes of the present invention can be represented as follows:

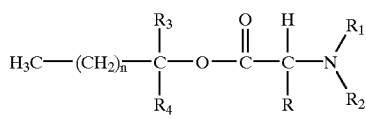

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_7$ alkyl; and $R_3$ and $R_4$ are members of the group consisting of hydrogen, methyl and ethyl.

Preferred penetration enhancers of this general type are the alkyl-2-(N,N-disubstituted amino)-alkanoates such as $C_4$- to $C_{18}$-alkyl (N,N-disubstituted amino)-acetates and $C_4$- to $C_{18}$-alkyl (N,N-disubstituted amino)-propionates. Exemplary specific alkyl-2-(N,N-disubstituted amino)-alkanoates include dodecyl 2-(N,N dimethylamino)-propionate (DDAIP);

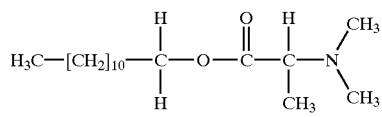

and dodecyl 2-(N,N-dimethylamino)-acetate (DDAA);

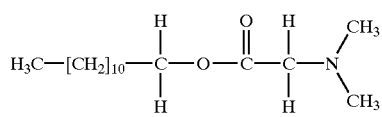

Alkyl-2-(substituted amino)-alkanoates are known. For example, dodecyl 2-(N,N-dimethylamino)-propionate (DDAIP) is available from Steroids, Ltd. (Chicago, Ill). In addition, alkyl-2-(N,N-disubstituted amino)-alkanoates can be synthesized from more readily available compounds as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

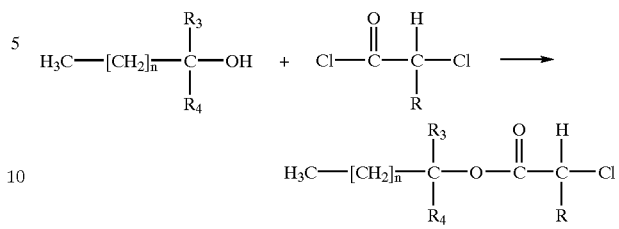

wherein R, $R_3$, $R_4$ and n are defined as above. The reaction temperature may be selected from about 10° C. to about 200° C. or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

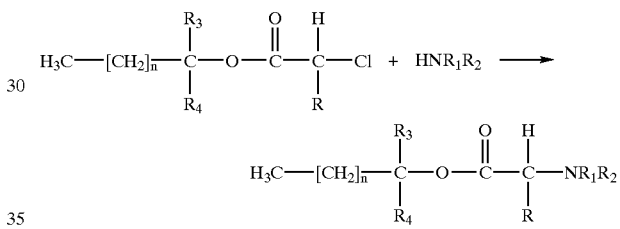

wherein n, R, $R_1$, $R_2$, $R_3$ and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical compound.

Suitable substituted amino alkanol alkanoates, i.e., (N-substituted amino)- and (N,N-disubstituted amino)-alkanol alkanoates, can be represented by the formula:

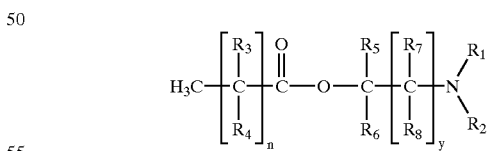

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are members of the group consisting of hydrogen, $C_1$ to $C_8$ alkyl, and $C_1$ to $C_3$ aryl; and $R_8$ is a member of the group consisting of hydrogen, hydroxyl, $C_1$ to $C_8$ alkyl, and $C_1$ to $C_8$ aryl.

Preferred (N,N-disubstituted amino)-alkanol alkanoates are $C_5$ to $C_{18}$ carboxylic acid esters. Exemplary specific (N,N-disubstituted amino)-alkanol alkanoates include 1-(N, N-dimethylamino)-2-propanol dodecanoate (DAIPD);

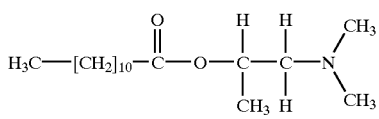

1-(N,N-dimethylamino)-2-propanol myristate (DAIPM);

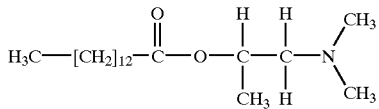

1-(N,N-dimethylamino)-2-propanol oleate (DAIPO);

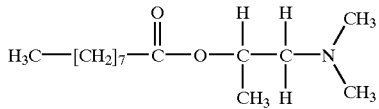

The foregoing (N-substituted amino)- and (N,N-disubstituted amino)-alkanol alkanoates are readily prepared by reacting the corresponding aminoalkanol with lauroyl chloride in the presence of triethylamine. A solvent such as chloroform is optional but preferred. For example, 1-(N,N-dimethylamino)-2-propanol can be reacted with lauroyl chloride in chloroform and in the presence of triethylamine to form 1-(N,N-dimethylamino)-2-propanol dodecanoate (DAIPD).

Acid addition salts of the aforementioned alkanoates, such as dodecyl 2-(N,N-dimethylamino)-propionate (DDAIP), can be inorganic as well as organic. Representative inorganic acid addition salts include the hydrochloric, hydrobromic, sulfuric, phosphoric, nitric acid addition salts, and their solvates. Exemplary organic acid addition salts include acetic, benzoic, salicylic, glycolic, succinic, nicotinic, tartaric, maleic, malic, pamoic, methanesulfonic, cyclohexanesulfamic, picric, and lactic acid addition salts, as well as their respective solvates.

A skin penetration enhancer which is an acid addition salt can be represented by the formula:

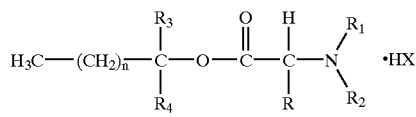

wherein n is an integer having a value in the range of about 4 to about 18; R is selected from the group consisting of hydrogen, $C_1$ to $C_7$ alkyl, benzyl and phenyl; $R_1$ and $R_2$ are selected from the group consisting of hydrogen and $C_1$ to $C_7$ alkyl; $R_3$ and $R_4$ are selected from the group consisting of hydrogen, methyl and ethyl; and HX is an acid.

Other acid addition salts suitable as skin penetration enhancers can be represented by the formula:

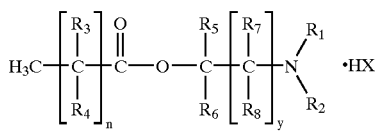

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are selected from the group consisting of hydrogen, $C_1$ to $C_8$ alkyl, and $C_1$ to $C_8$ aryl; $R_8$ is selected from the group consisting of hydrogen, hydroxyl, $C_1$ to $C_8$ alkyl, and $C_1$ to $C_8$ aryl; and HX is an acid.

Preferred among the inorganic acid addition salts are DDAIP hydrogen chloride,

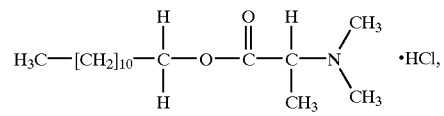

and DDAIP dihydrogen sulfate,

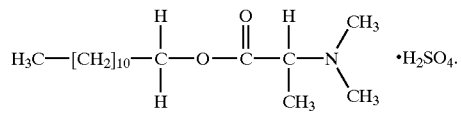

As stated hereinabove, alkyl-2-(N,N-disubstituted amino)-alkanoates such as DDAIP can be synthesized from readily available starting materials as described in U.S. Pat. No. 4,980,378 to Wong et al. In the first step, long chain alkyl halogenoacetates are prepared by reaction of the corresponding long chain alkanols with halogenomethyl halogenoformates or the like in the presence of an appropriate base such as triethylamine, typically in a suitable solvent such as chloroform. For DDAIP, this reaction can be depicted as follows:

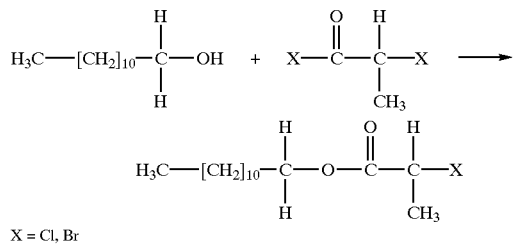

X = Cl, Br

The reaction temperature may be selected from about 10° Celsius to about 200° Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the alkyl substituted halogenoacetate is condensed with an appropriate amine according to the scheme:

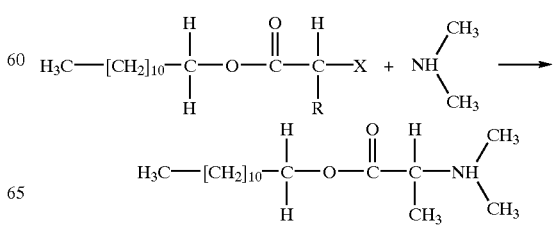

X = Cl, Br

Excess amine reactant is typically used as the base and the reaction is conveniently conducted in a suitable solvent such as ether. This second step is preferably run at room temperature, although temperature may vary. Reaction time usually varies from about one hour to several days.

An alternate and preferred approach to synthesizing DDAIP is the transesterification of ethyl 2-(N,N-dimethylamino)-propionate. Ethyl 2-(N,N-dimethylamino)-propionate can be prepared by reacting commercially available ethyl 2-bromopropionate with dimethylamine followed by distillation to separate unreacted halogenated compounds.

To trigger the transesterification, the ethyl 2-(N,N-dimethylamino)-propionate is heated in the presence of 1-dodecanol and a basic transesterification catalyst such as sodium methoxide. Other suitable basic transesterification catalysts are n-butyl lithium, potassium cyanide, and the like.

Also suitable as transesterification catalysts are acids such as sulfuric acid, p-toluene sulfuric acid, and the like. Still other transesterification catalysts that can be used are boron tribromide, trimethylsilyl iodide, trimethylsilyl iodine, aluminum oxide, tetraisopropyl titanate, molecular sieves containing tert-butanol and potassium tertiary butoxide, Grignard reagents, porcine pancreatic lipase, pig liver esterase, horse liver esterase (with solid support), -chymotrypsin, silver trifluoroacetate, mercury(II) trifluoroacetate, palladium(II) chloride, mercury(II) acetate with sulfuric acid, mercury(II) chloride (cadmium carbonate), thallium (II) trifluoro acetate, and compounds of the formula X—Sn (n—Bu)$_2$—O—Sn(n—Bu)$_2$—OH, where X is a halogen.

A representative reaction scheme follows:

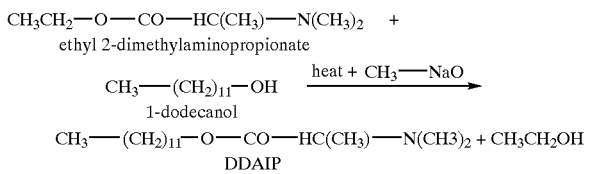

The ethyl 2-(N,N-dimethylamino)-propionate is preferably refluxed for about 2 hours in the presence of 10 percent stoichiometric excess 1-dodecanol and a catalytic amount of sodium methoxide (predissolved in toluene). During this process, the ethanol formed is removed from the reaction medium by azeotropic distillation. Following the reaction phase, the solids of the remaining mixture are filtered off, resulting in a DDAIP filtrate.

The transesterification approach to synthesizing DDAIP results in a product containing relatively lower levels of by-products and unreacted reactants, which are undesirable, often skin-irritating, and difficult to remove by conventional methods.

To make an acid addition salt, DDAIP free base is mixed with a water immiscible solvent such as hexane to form a reactant solution. The reactant solution is maintained at a temperature in the range of about 100 to about −10° Celsius. Acid is then added to the temperature-controlled solution in an amount sufficient for the formation of a salt precipitate in the reactant solution. During the acid addition, constant stirring (or agitation) of the reactant solution is optional, but preferred. The salt precipitate of DDAIP is recovered by any suitable method such as filtration.

The foregoing method of making DDAIP salts may be utilized as a purification step for removing reaction by-products and unprocessed reactants from DDAIP. Synthesis procedures according to the present invention can result in substantially pure salt precipitates of DDAIP that can be incorporated into the compositions of the present invention.

The penetration enhancer is present in an amount sufficient to enhance the penetration of the prostaglandin $E_1$. The specific amount varies necessarily according to the desired release rate and the specific form of prostaglandin $E_1$ used. Generally, this amount ranges from about 0.5 percent to about 10 percent, based on the total weight of the composition. Preferably, the penetration enhancer is about 5 weight percent of the composition.

Polysaccharide gums are also an important ingredient to the present composition. Suitable representative gums are those in the galactomannan gum category. A galactomannan gum is a carbohydrate polymer containing D-galactose and D-mannose units, or other derivatives of such a polymer. There is a relatively large number of galactomannans, which vary in. composition depending on their origin. The galactomannan gum is characterized by a linear structure of β-D-mannopyranosyl units linked (1–4). Single membered α-D-manopyranosyl units, linked (1–6) with the main chain, are present as side branches. Galactomannan gums include guar gum, which is the pulverized endosperm of the seed of either of two leguminous plants (*cyamposis tetragonalobus* and *psoraloids*) and locust bean gum, which is found in the endosperm of the seeds of the carobtree (*ceratonia siliqua*). Locust bean gum is preferred for the present invention.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums: Polysaccharides & Their Derivatives*, Whistler R. L. and BeMiller J. N. (eds.), 3rd Ed. Academic Press (1992) and Davidson R. L., *Handbook of Water-Soluble Gums & Resins*, McGraw-Hill, Inc., N.Y. (1980). Most gums are commercially available in various forms, commonly a powder, and ready for use in foods and topical compositions. For example, locust bean gum in powdered form is available from Tic Gums Inc. (Belcam, M.d).

The polysaccharide gums are present in the range from about 0.5 percent to about 5 percent, based on the total weight of the composition, with the preferred range being from 0.5 percent to 2 percent. Illustrative compositions are given in the examples, below.

An optional alternative to the polysaccharide gum is a polyacrylic acid polymer. A common variety of polyacrylic acid polymer is known generically as "carbomer." Carbomer is polyacrylic acid polymers lightly cross-linked with poly-alkenyl polyether. It is commercially available from the B. F. Goodrich Company (Akron, Ohio) under the designation "CARBOPOL®." A particularly preferred variety of carbomer is that designated as "CARBOPOL 940."

Other polyacrylic acid polymers suitable for use in practicing this invention are those commercially available under the designations "Pemulen®" (B. F. Goodrich Company) and "POLYCARBOPHIL™" (A. H. Robbins, Richmond, Va.). The Pemulen® polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ enhancer is a polyacrylic acid cross-linked with divinyl glycol.

Where polyacrylic acid polymers are present, they represent about 0.5 percent to about 5 percent of the composition, based on its total weight.

Another important component of the present invention is a lipophilic compound. The term lipophilic compound as used herein refers to an agent that is both lipophilic and hydrophilic. The $C_1$ to $C_8$ aliphatic alcohols, the $C_2$ to $C_{30}$ aliphatic esters, and their mixtures can serve as a lipophilic compound. Illustrative suitable alcohols are ethanol, n-propanol and isopropanol, while suitable esters are ethyl acetate, butyl acetate, ethyl laurate, methyl propionate and isopropyl myristate. As used herein, the term "aliphatic alcohol" includes polyols such as glycerol, propylene glycol and polyethylene glycols. A mixture of alcohol and ester is preferred, and in particular, a mixture of ethanol and ethyl laurate myristate is most preferred.

The concentration of lipophilic compound required necessarily varies according to other factors such as the desired semi-solid consistency and the desired skin penetration promoting effects. The preferred topical composition contains lipophilic compound in the range of 7 percent to 40 percent by weight based on the total weight of the composition. Where a mixture of aliphatic alcohol and aliphatic ester are employed, the preferred amount of alcohol is in the range of 5 percent to 15 percent, while that of aliphaticester is in the range from 2 percent to 15 percent (again based on the total weight of the composition).

An optional, but preferred, component of the present invention is an emulsifier. Although not a critical factor, a suitable emulsifier generally will exhibit a hydrophilic-lipophilic balance number greater than 10. Sucrose esters, and specifically sucrose stearate, can serve as emulsifiers for the topical composition of the present invention. Sucrose stearate is a well known emulsifier available from various commercial sources. When an emulsifier is used, sucrose stearate present up to about 2 percent, based on the total weight of the composition, is preferred. The preferred amount of sucrose stearate emulsifier can also be expressed as a weight ratio of emulsifier to polysaccharide gum. A ratio of 1 to 6 emulsifier to gum is preferred, and a ratio of 1 to 4 is most preferred to generate the desired semi-solid consistency and separation resistance.

The present invention includes an acid buffer system. Acid buffer systems serve to maintain or buffer the pH of compositions within a desired range. The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known. While there are countless suitable buffers, potassium phosphate monohydrate has proven effective for compositions of the present invention.

The final pH value of the pharmaceutical composition of the present invention may vary within the physiologically compatible range. Necessarily, the final pH value is not irritating to human skin. Without violating this constraint, the pH may be selected to improve prostaglandin $E_1$ stability and to adjust consistency when required. With these factors accounted for, the preferred pH value is about 3.0 to 7.4. The most preferred pH range is from about 3.5 to about 6.0.

The remaining component of the composition is water, which is necessarily purified. The composition contains water in the range of about 50 to about 90 percent, based on the total weight of the composition. The specific amount of water present is not critical, however, being adjustable to obtain the desired consistency and/or concentration of the other components.

Additionally, known transdermal penetration enhancers can also be added, if desired. Illustrative are dimethyl sulfoxide (DMSO), dimethyl acetamide (DMA), 2-pyrrolidone, N,N-diethyl-m-toluamide (DEET), 1-dodecylazacycloheptane-2-one (Azone®, a registered trademark of Nelson Research), N,N-dimethylformamide, N-methyl-2-pyrrolidone, calcium thioglycolate, oxazolidinone, dibxolane derivatives, laurocapram derivatives, and macrocyclic enhancers such as macrocyclic ketones.

Prostaglandin $E_1$ stabilizers, coloring agents, rheological agents, and preservatives can be added to the extent that they do not overly limit prostaglandin $E_1$ skin penetration or prevent the desired semi-solid consistency.

Contemplated dosage forms of the semi-solid pharmaceutical composition of the present invention are creams, gels, and the like, also including but not limited to compositions suitable for use with transdermal patches and like devices.

The ingredients listed above may be combined in any order and manner that produces a stable composition comprising a prostaglandin $E_1$ evenly dispersed throughout a semi-solid formulation. One available approach to preparing such compositions involves evenly dispersing the polysaccharide gum (or polyacrylic acid) in a premixed water/buffer solution and then thoroughly homogenizing (i.e. mixing) the resulting mixture, which will be labelled "Part A." When present, the emulsifier is added to the water/buffer solution before dispersing the polysaccharide gum. Any suitable method of adjusting the pH value of Part A to the desired-level may be used, for example, by adding concentrated phosphoric acid or sodium hydroxide.

Separately, the prostaglandin $E_1$ is dissolved with agitation in the lipophilic compound, which itself may be a mixture of alcohols, esters, or alcohol with ester. Next, the penetration enhancer is added. Alternatively, when the lipophilic compound includes both an alcohol and. an ester, the prostaglandin $E_1$ can be dissolved in the alcohol before adding the penetration enhancer followed by the ester. In either case, the resulting mixture will be labelled "Part B." The final step involves slow addition (.e.g. dropwise) of Part B into Part A under constant mixing.

The resulting topical composition exhibits the advantageous properties described above, including improved prostaglandin $E_1$ permeation and bioavailability without drug overloading, reduced skin damage and related inflammation, and increased flexibility in design of dosage forms. These compositions can be used for prolonged treatment of peripheral vascular disease, male impotency and other disorders treated by prostaglandin $E_1$, while avoiding the low bioavailability and rapid chemical decomposition associated with other delivery methods. Application of prostaglandin $E_1$ in a topical composition of the present invention to the skin of a patient allows a predetermined amount of prostaglandin $E_1$ to be administered continuously to the patient and avoids undesirable effects present with a single or multiple administrations of larger dosages by injection. By maintaining a sustained dosage rate, the prostaglandin $E_1$ level in the patient's target tissue can be better maintained within the optimal therapeutic range.

The practice of the present invention is demonstrated in the following examples. These examples are meant to illustrate the invention rather than to limit its scope. Variations in the treating compositions which do not adversely affect the effectiveness of prostaglandin $E_1$ will be evident to one skilled in the art, and are within the scope of this invention. For example, additional ingredients such as coloring agents, anti-microbial preservatives, emulsifiers, perfumes, prostaglandin $E_1$ stabilizers, and the like may be included in the compositions as long as the resulting composition retains desirable properties, as described above. Unless otherwise indicated, each composition is prepared by conventionally admixing the respective indicated components together.

EXAMPLE 1

Topical Prostaglandin $E_1$ Composition A

Composition A was prepared as follows. Part A was formed by dissolving 0.4 parts prostaglandin $E_1$ (Alprostadil USP) in 5 parts ethyl alcohol. Next, 5 parts dodecyl 2-(N, N-dimethylamino)-propionate were mixed into the alcohol-prostaglandin $E_1$ solution, followed by 5 parts ethyl laurate.

Part B was prepared starting from a pH 5.5 water/buffer solution. The water/buffer solution was prepared by adding sufficient potassium phosphate monohydride to purified water to create a 0.1 M solution. The pH of the water/buffer solution was adjusted to 5.5 with a strong base solution (1 N sodium hydroxide) and a strong acid (1 N phosphoric acid). The buffer solution represented about 80 parts of the total composition.

To the buffer solution, was added 0.5 parts ethyl laurate. Next, the locust bean gum (in powder form) was dispersed in the buffer solution and homogenized using a homogenizer. TABLE 1, below, contains a list of ingredients.

The resulting composition was a spreadable, semi-solid suitable for application to the skin without the need for supporting devices such as patches and adhesive strips. The composition was both homogenous in appearance and resistant to separation.

Composition A was evaluated for skin penetration using shed snake skin as a model barrier. Shed snake skin was obtained from the Animal Care Unit of the University of Kansas. With head and tail sections removed, the skin was randomly divided into test sections and then hydrated by soaking.

The samples were then evaluated using Franz-type Diffusion Cells (surface are 1.8 cm$^2$) Specifically, skin pieces were mounted on top of a receptor cell of a vertical diffusion cell assembly in which a small magnetic bar was inserted and filled with an isotonic buffer. A seal was placed on top of the skin section followed by a donor cell. The two cells were clamped together. Known amounts of the formulations were applied on the bottom of a small capped vial (weight ≈5 grams) which fits exactly to the donor cell to ensure uniform distribution. The vials were placed on the skin in the donor cell. To reduce the evaporation of the ingredients, the donor cell and vial were gently taped together with a water-resistant adhesive band. The cells were transferred to a stirred water bath (32° C.). Samples were withdrawn from the cells each hour for four hours and analyzed for the concentration of prostaglandin $E_1$, with changes in concentration indicating the amount penetrating. Tests with multiple skin samples yielded data that were averaged.

For a discussion of the use of shed snake skin in the evaluation of drug penetration, see U.S. Patent No. 4,771,004 to Higuchi, which is incorporated here by reference to the extent that it is not inconsistent.

The prostaglandin $E_1$ penetrated quickly at a relatively sustained rate for four hours. The results of the penetration study are presented in TABLE 2, below, and in FIG. 1.

EXAMPLE 2

Topical Prostaglandin $E_1$ Composition B

Composition B was prepared using the ingredients listed in TABLE 1, below. Composition B contained more prostaglandin $E_1$ than Composition A. Despite this increased drug loading, Composition B exhibited a similar semi-solid consistency and homogenous appearance. The penetration of prostaglandin $E_1$ was measured according to the technique described in Example 1. Composition B provided a relatively fast, sustained delivery of prostaglandin $E_1$. The results are presented in TABLE 2, below, and in FIG. 1.

EXAMPLE 3

Topical Prostaglandin $E_1$ Composition C

Composition C was prepared using the ingredients listed in TABLE 1, below. Composition B contained more prostaglandin $E_1$ than either Composition A or B. The increased drug loading had little or no effect on the consistency or appearance, which substantially matched that of Compositions A and B. The penetration of prostaglandin $E_1$ was again measured according to the technique described in Example 1. According to this test, Composition C also provided a relatively fast, sustained delivery of prostaglandin $E_1$. The results are presented in TABLE 2, below, and in FIG. 1.

EXAMPLE 4

Topical Prostaglandin $E_1$ Composition D

Composition D was prepared using the ingredients listed in TABLE 1, below. The level of prostaglandin $E_1$ was again increased without substantially affecting the favorable consistency and separation resistance. The penetration of prostaglandin $E_1$ was again measured according to the technique described in Example 1. The results are presented in TABLE 2, below, and in FIG. 1.

EXAMPLE 5

Topical Prostaglandin $E_1$ Composition E

Composition E was prepared using the ingredients listed in TABLE 1, below. To assess the repeatability of compositions according to the present invention, the recipe of Composition D was again applied for Composition E. Repeatability was substantially confirmed by Composition E's favorable, semi-solid consistency and separation resistance. The penetration of prostaglandin $E_1$ was again measured according to the technique described in Example 1. The prostaglandin $E_1$ delivery from Composition E was again relatively fast and sustained. The results are presented in TABLE 2, below, and in FIG. 1.

EXAMPLE 6

Topical Prostaglandin $E_1$ Composition F

The level of prostaglandin $E_1$ was again increased for Composition F. The specific ingredients are listed in TABLE 1. The favorable consistency and separation resistance was undiminished. The results of a penetration analysis are presented in TABLE 2, below, and in FIG. 1.

EXAMPLE 7

Topical Prostaglandin $E_1$ Composition G

Composition G was prepared using the ingredients listed in TABLE 1. For Composition G, the recipe of Composition F was repeated except that the ester component (ester laurate) was omitted and the level of ethanol was increased a corresponding amount. The resulting composition was also a spreadable, semi-solid having a homogenous appearance and resistance to separation. The results of a penetration analysis are presented in TABLE 2, below, and in FIG. 1. While still favorable, these results reflect the relative benefit to compositions of the present invention from a lipophilic compound that includes both an ester component and an alcohol component.

TABLE 1

Topical Prostaglandin $E_1$ Compositions

| Ingredient (wt %) | | A | B | C | D | E | F | G |
|---|---|---|---|---|---|---|---|---|
| Part A: | prehydrated locust bean gum | 3 | 3 | 3 | 3 | 3 | 3 | 3 |
| | water/buffer (pH 5.5) | 81 | 81 | 81 | 81 | 81 | 81 | 81 |
| | sucrose stearate | 0.5 | 0.5 | 0.5 | 0.5 | 0.5 | 0.5 | 0.5 |
| Part B: | prostaglandin $E_1$ | 0.1 | 0.2 | 0.3 | 0.4 | 0.4 | 0.5 | 0.4 |
| | DDAIP | 5 | 5 | 5 | 5 | 5 | 5 | 5 |
| | ethanol | 5 | 5 | 5 | 5 | 5 | 5 | 10 |
| | ethyl laurate | 5 | 5 | 5 | 5 | 5 | 5 | — |

EXAMPLE 8

Comparison of Penetration Profiles

TABLE 2 shows the cumulative amount of prostaglandin $E_1$ penetrating each hour for 4 hours for each example composition according to the present invention. These data demonstrate the ability of the present invention to delivery prostaglandin $E_1$ drugs transdermally.

FIG. 1 is a graph generated from the data presented in TABLE 2 Significantly, and well represented in graphical form, compositions according to the present invention deliver effective skin penetration relatively fast and at a sustained rate. As expected, cumulative penetration increases with increased prostaglandin $E_1$ loading of the source composition.

TABLE 2

Cumulative Prostaglandin $E_1$ Penetration ($\mu g/cm^2$)

| Hour | A | B | C | D | E | F | G |
|---|---|---|---|---|---|---|---|
| 1 | 1.96 | 3.37 | 5.47 | 7.20 | 7.09 | 10.38 | 3.03 |
| 2 | 5.49 | 9.72 | 18.06 | 21.26 | 16.6 | 25.03 | 8.17 |
| 3 | 11.25 | 18.18 | 30.34 | 35.53 | 28.24 | 42.18 | 12.93 |
| 4 | 13.98 | 23.48 | 38.49 | 47.98 | 41.1 | 52.13 | 18.71 |

To further assess the effectiveness of compositions according the present invention, comparative example compositions were prepared. For a first comparative example (Comparative Example 1) was prepared with the same recipe as Compositions D and E except that the DDAIP penetration enhancer was omitted. A second comparative example (Comparative Example 2), the DDAIP was again omitted, but the level of ethanol was increased a corresponding amount. The specific ingredients used are listed in TABLE 3, below.

TABLE 3

Comparative Examples

| Ingredient (wt %) | | Comparative Composition 1 | Comparative Composition 2 |
|---|---|---|---|
| Part A: | prehydrated locust bean gum | 3 | 3 |
| | water/buffer (pH 5.5) | 86 | 81 |
| | sucrose stearate | 0.5 | 0.5 |
| Part B: | prostaglandin $E_1$ | 0.4 | 0.4 |
| | ethanol | 5 | 10 |
| | ethyl laurate | 5 | 5 |

The penetration of prostaglandin $E_1$ from was evaluated according to the technique described in Example 1. The results are presented in TABLE 4, below.

TABLE 4

Comparative Examples
Cumulative Prostaglandin $E_1$ Penetration ($\mu g/cm^2$)

| Hour | Comparative Composition 1 | Comparative Composition 2 |
|---|---|---|
| 1 | 2.64 | 1.55 |
| 2 | 4.46 | 3.69 |
| 3 | 6.59 | 6.63 |
| 4 | 9.67 | 11.05 |

The data of TABLE 4 are compared graphically to the example compositions having the same prostaglandin $E_1$ loading, Compositions D and E. The penetration data demonstrate that compositions according to the present invention benefit greatly from the presence of the DDAIP penetration enhancer. DDAIP.HCl or DDAIP.$H_2SO_4$ can be used in the aforementioned compositions in lieu of DDAIP free base.

EXAMPLE 9

Preparation Of Hydrochloric Acid Addition Salt Of DDAIP

DDAIP was prepared by transesterification of ethyl 2-(N, N-dimethylamino)-propionate obtained from Varsal Instruments Inc. (Warminster, Pa.). Specifically, a mixture ethyl 2-(N,N-dimethylamino)-propionate, 1-dodecanol, and sodium methoxide predissolved in toluene was refluxed for about 2 hours. As ethanol formed, it was removed by azeotropic distillation. After about 2 hours of refluxing, the remaining reaction product was filtered to remove solids.

DDAIP.HCl was prepared by diluting 50 grams of the DDAIP filtrate with 200 milliliters of hexane in a flask, where the hexane and DDAIP were thoroughly mixed. The resulting hexane-DDAIP mixture was cooled to about 5° Celsius. Next, under constant stirring, hydrogen chloride gas was bubbled through the mixture for approximately 2 to 5 minutes, after which a precipitate was noted. The resulting precipitate was recovered by filtration. About 49 grams of precipitate were recovered.

Samples of the recovered substance were analyzed for carbon-nitrogen-hydrogen content, melting point, X-ray powder diffraction spectra, mass spectra, infrared spectra, and nuclear magnetic resonance (NMR) in the $^1H$ and the $^{13}C$ modes. Before property testing, the recovered precipitate was dissolved in boiling ethyl acetate and then recrystallized by allowing the mixture to cool to room temperature.

An elemental carbon-nitrogen-hydrogen analysis detected 63.29 percent carbon, 4.26 percent nitrogen, and 11.34 percent hydrogen, which generally matched the calculated values of 63.4 percent carbon, 4.3 percent nitrogen and 11.2 percent hydrogen for DDAIP.HCl ($C_{17}H_{35}NO_2 \cdot HCl$). Melting point was tested and verified to be in the range of about 88° to about 90° Celsius.

For x-ray powder diffraction testing, a ground sample of DDAIP.HCl was tested using a Siemens D500 Automated Powder Diffractometer equipped with a graphite monochromator and a Cu ($\lambda=1.54$ Å) x-ray source operated at 50 kV and 40 mA. The two-theta scan range was 40 to 40° with a step scan window of 0.05° per 1.2 seconds. Beam slits were set at No. (1)1°, (2)1°, (3)1°, (4)0.15°, and (5)0.15° widths. Well-defined peaks were detected at the following values of two-theta: 19.5°, 21°, 25°, 29.6°.

Mass spectroscopy of a sample dissolved in dichloromethane produced peaks for the largest molecules detected at unit masses of 284 and 286, which compares well to the molecular weight of a DDAIP molecule, about 285.47.

Figure 3:
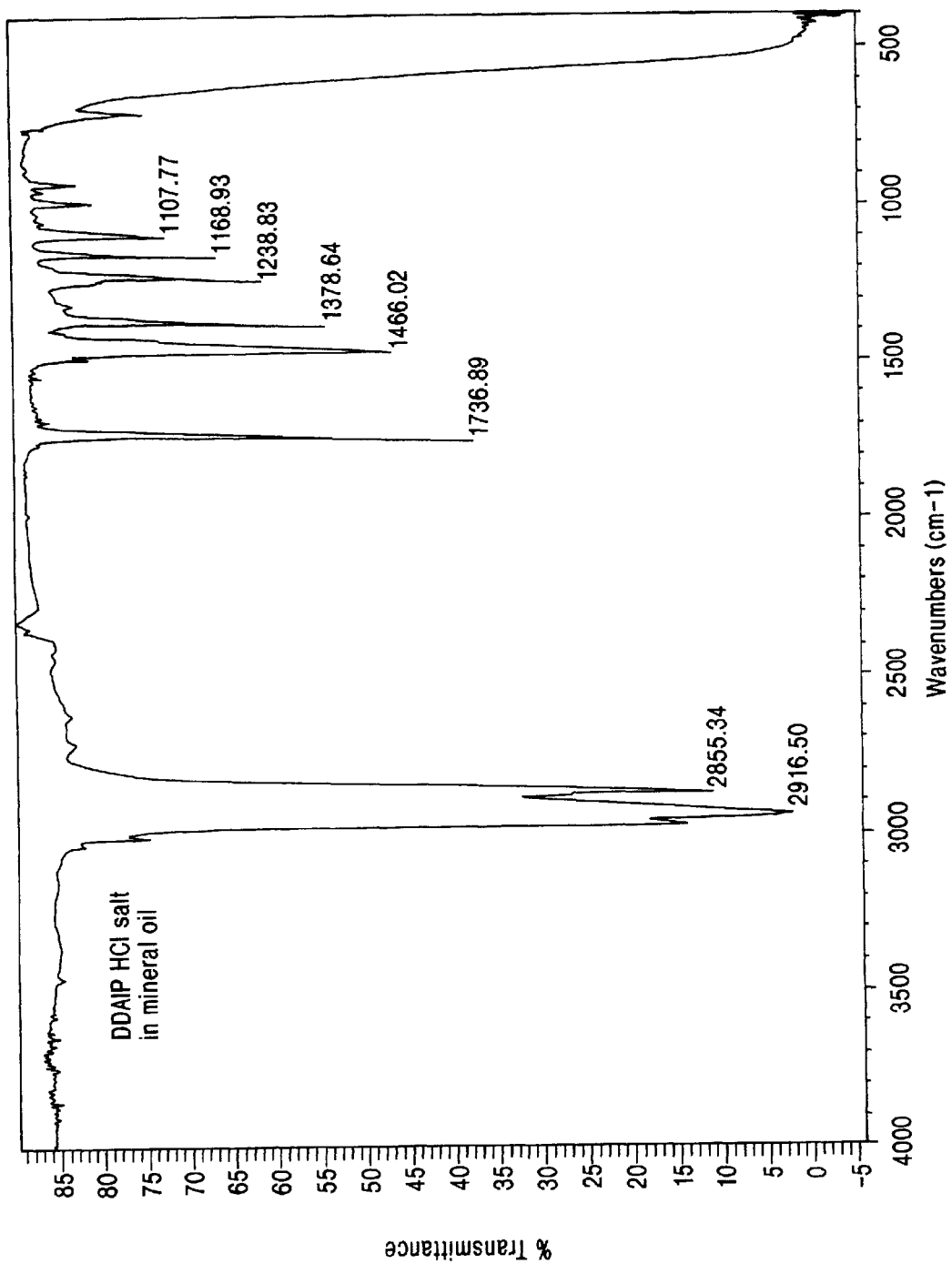
FIG. 3 is an infrared spectrum of a sample of a crystalline hydrochloric acid addition salt of DDAIP (DDAIP.HCl) dispersed in mineral oil.

The results of an infrared spectroscopy analysis of a DDAIP.HCl sample (in mineral oil) are presented in FIG. 3. Data generated by NMR analysis for $^1H$ and $^{13}C$ spectra did not reveal shifts that are inconsistent with DDAIP.HCl.

EXAMPLE 10

Preparation Of Sulfuric Acid Addition Salt Of DDAIP

DDAIP.$H_2SO_4$ was prepared by mixing 200 milliliters hexane with 50 grams of DDAIP prepared as described in Example 9 in a flask, where the hexane and DDAIP were thoroughly mixed together. The resulting hexane-DDAIP mixture was cooled to about 50 Celsius. Concentrated sulfuric acid was then added dropwise under constant stirring to form a precipitate. After adding about 18 grams of sulfuric acid, the stirring was discontinued and the resulting DDAIP.$H_2SO_4$ precipitate was separated by filtration. About 60 grams of precipitate were recovered.

Samples were analyzed by the same methods listed in Example 9. Before property testing, the DDAIP.$H_2SO_4$ was dissolved in boiling ethyl acetate and recrystallized.

Elemental analysis indicated 53.41 percent carbon, 3.63 percent nitrogen and 9.61 percent hydrogen. These values generally matched the calculated values of 53.23 percent carbon, 3.65 percent nitrogen, 9.72 percent hydrogen for DDAIP.$H_2SO_4$ ($C_{17}H_{37}NO_6S$). Melting point was tested and verified to be in the range of about 58° to about 60° Celsius.

For x-ray powder diffraction, a ground sample of DDAIP.$H_2SO_4$ was tested using the diffractometer and equipment settings described in Example 9. Well-defined peaks were detected at the following values of two-theta: 13.3°, 16.6°, 21.8°, 23.3°.

Figure 4:
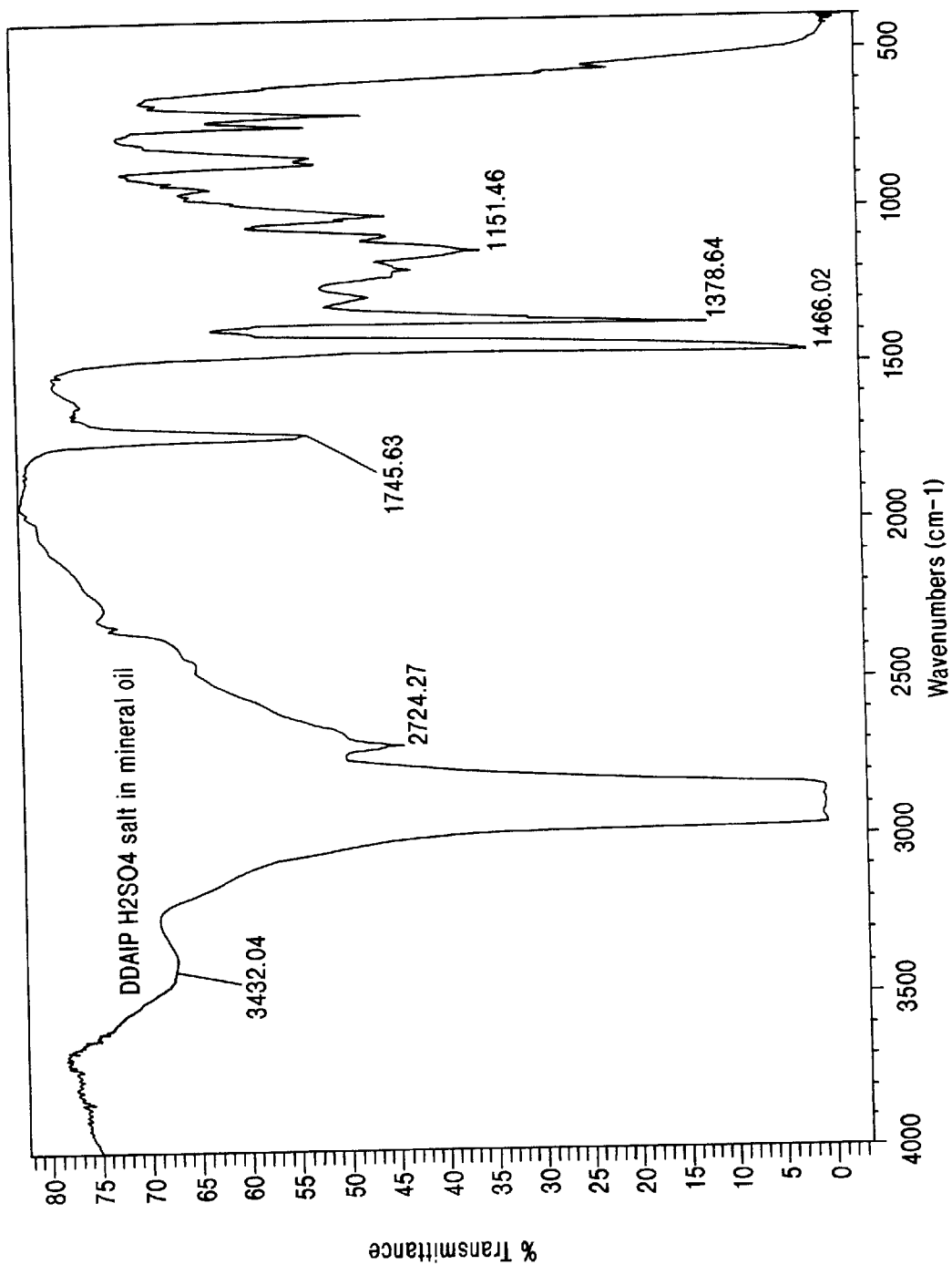
FIG. 4 is an infrared spectrum of a sample of a crystalline sulfuric acid addition salt of DDAIP (DDAIP.H₂SO₄) dispersed in mineral oil.

Mass spectroscopy of a sample in dichloromethane produced peaks for the largest molecules detected at unit masses of 284 and 286, which compares well to the molecular weight of DDAIP, about 285.47. The results from an infrared spectroscopy analysis are presented in FIG. 4. Data generated by NMR analysis for $^1H$ and $^{13}C$ spectra did not reveal shifts that are inconsistent with DDAIP.$H_2SO_4$.

The foregoing specification is intended as illustrative and is not to be taken as limiting. Still other variations within the spirit and the scope of the invention are possible and will readily present themselves to those skilled in the art.

We claim:

1. A topical composition which comprises:
   prostaglandin $E_1$;
   a skin penetration enhancer which is an acid addition salt of a compound selected from the group consisting of an alkyl-2-(substituted amino)-alkanoate, a (substituted amino)-alkanol alkanoate, and a mixture thereof;
   a polysaccharide gum;
   a lipophilic compound which is selected from the group consisting of an aliphatic $C_1$ to $C_8$ alcohol, an aliphatic $C_8$ to $C_{30}$ ester, and a mixture thereof; and
   an acidic buffer system providing a buffered pH value for said composition in the range of about 3 to about 7.4.

2. The topical composition in accordance with claim 1 wherein said penetration enhancer is an alkanoate represented by the formula:

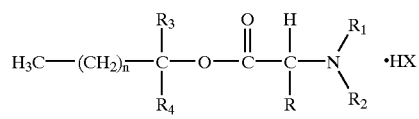

wherein n is an integer having a value in the range of about 4 to about 18; R is a selected from the group consisting of hydrogen, $C_1$ to $C_7$ alkyl, benzyl and phenyl; $R_1$ and $R_2$ are selected from the group consisting of hydrogen and $C_1$ to $C_7$ alkyl; $R_3$ and $R_4$ are selected from the group consisting of hydrogen, methyl and ethyl; and HX is an acid.

3. The topical composition in accordance with claim 1 wherein said penetration enhancer is an acid addition salt of a $C_4$ to $C_{18}$, alkyl (N,N-disubstituted amino)-acetate.

4. The topical composition in accordance with claim 1 wherein said penetration enhancer is an acid addition salt of dodecyl (N,N-dimethylamino)-acetate.

5. The topical composition in accordance with claim 1 wherein said penetration enhancer is an acid addition salt of dodecyl 2-(N,N-dimethylamino)-propionate.

6. The topical composition in accordance with claim 1 wherein said penetration enhancer is dodecyl 2-(N,N-dimethylamino)-propionate hydrochloride.

7. The topical composition in accordance with claim 1 wherein said penetration enhancer is dodecyl 2-(N,N-dimethylamino)-propionate hydrogen sulfate.

8. The topical composition in accordance with claim 1 wherein said penetration enhancer is an alkanoate represented by the formula:

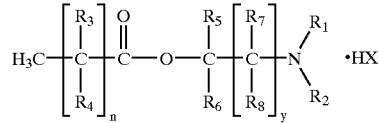

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are selected from the group consisting of hydrogen, $C_1$ to $C_8$ alkyl, and $C_1$ to $C_8$ aryl; $R_8$ is selected from the group consisting of hydrogen, hydroxyl, $C_1$ to $C_8$ alkyl, and $C_1$ to $C_8$ aryl; and HX is an acid.

9. The topical composition in accordance with claim 1 wherein said penetration enhancer is an acid addition salt of a $C_5$ to $C_{18}$ carboxylic acid ester.

10. The topical composition in accordance with claim 1 wherein said penetration enhancer is an acid addition salt of 1-(N,N-dimethylamino)-2-propanol dodecanoate.

11. The topical composition in accordance with claim 1, wherein said penetration enhancer is an acid addition salt of 1-(N,N-dimethylamino)-2-propanol myristate.

12. The topical composition in accordance with claim 1 wherein said penetration enhancer is an acid addition salt of 1-(N,N-dimethylamino)-2-propanol oleate.

13. The topical composition in accordance with claim 1 wherein said polysaccharide gum is a galactomannan gum.

14. The topical composition in accordance with claim 13 wherein said galactomannan gum is a locust bean gum.

15. The topical composition in accordance with claim 13 wherein said galactomannan gum is a guar gum.

16. The topical composition in accordance with claim 1 wherein said lipophilic compound is ethanol.

17. The topical composition in accordance with claim 1 wherein said lipophilic compound is a polyol aliphatic alcohol.

18. The topical composition in accordance with claim 1 wherein said lipophilic compound is isopropyl myristate.

19. The topical composition in accordance with claim 1 wherein said lipophilic compound is ethyl laurate.

20. The topical composition in accordance with claim 1 wherein said lipophilic compound is a mixture of ethanol and isopropyl myristate.

21. The topical composition in accordance with claim 1 wherein said lipophilic compound is a mixture of ethanol and ethyl laurate.

22. The topical composition in accordance with claim 1 wherein said penetration enhancer is dodecyl 2-(N,N-dimethylamino)-propionate hydrochloride, said polysaccharide gum is a locust bean gum, and said lipophilic compound is a mixture of ethanol and ethyl laurate.

23. A topical composition in accordance with claim 1 wherein said polysaccharide gum is 0.5 to 5 weight percent locust bean gum, said penetration enhancer is 0.5 to 25 weight percent dodecyl 2-(N,N-dimethylamino)-propionate hydrochloride, and said lipophilic compound is a mixture of 0.5 to 80 weight percent ethanol and 0.5 to 80 weight percent isopropyl myristate, based on the total weight of the composition.

24. A topical composition in accordance with claim 1 wherein said polysaccharide gum is 0.5 to 5 weight percent locust bean gum, said penetration enhancer is 0.5 to 5 weight percent dodecyl 2-(N,N-dimethylamino)-propionate hydrochloride, and said lipophilic compound is a mixture of 0.5 to 25 weight percent ethanol and 0.5 to 25 weight percent ethyl laurate, based on the total weight of the composition.

25. A topical composition in accordance with claim 1, which further contains an emulsifier.

26. A topical composition in accordance with claim 24 wherein said emulsifier is an sucrose ester.

27. A topical composition in accordance with claim 24 wherein said emulsifier is sucrose stearate.

28. A topical prostaglandin composition which comprises:

prostaglandin $E_1$;

a skin penetration enhancer which is an acid addition salt of a compound selected from the group consisting of an alkyl-2-(substituted amino)-alkanoate, a (substituted amino)-alkanol alkanoate, and a mixture thereof;

a polyacrylic acid polymer;

a lipophilic compound which is selected from the group consisting of an aliphatic $C_1$ to $C_8$ alcohol, an aliphatic $C_8$ to $C_{30}$ ester, and a mixture thereof; and an acidic buffer system providing a buffered pH value for said composition in the range of about 3 to about 7.4.

29. A topical composition in accordance with claim 28 wherein said polyacrylic acid polymer is a carbomer.

* * * * *